United States Patent [19]

Voth et al.

[11] Patent Number: Plant 5,265

[45] Date of Patent: Jul. 31, 1984

[54] STRAWBERRY PLANT 'TUSTIN'

[75] Inventors: Victor Voth, Santa Ana; Royce S. Bringhurst, Davis, both of Calif.

[73] Assignee: The Regents of the University of California, Berkeley, Calif.

[21] Appl. No.: 452,695

[22] Filed: Dec. 23, 1982

[51] Int. Cl.[3] ..... A01H 5/03

[52] U.S. Cl. ..... Plt./48

[58] Field of Search ..... Plt./48

*Primary Examiner*—Robert E. Bagwill

*Attorney, Agent, or Firm*—Townsend and Townsend

[57] ABSTRACT

A new and distinct variety of strawberry plant of the short-day type which performs well in both summer and winter plantings, characterized by its semi-compact growth, prolificy in runner production in nursery plantings and its self fertile flowers borne on long semi-erect peduncles. The variety is further characterized by its large sized fruit, blunt medium conic to wedgy in shape. The fruit is slightly hollow internally and has a light ring around its core. Fruit flavor compares favorably with the best of California varieties now in use and firmness and durability of the fruit make it suitable for both fresh and processing markets.

3 Drawing Figures

DESCRIPTION

This invention relates to a new and distinctive short-day type strawberry cultivar designated as 'Tustin' which is the result of a cross of 'Douglas' (U.S. Plant Pat. No. 4,487)×Cal 72.361-105-C55 (U.S. Plant Pat. No. 4,481).

'Tustin' first fruited at the University of California South Coast Field Station, Santa Ana in 1979 where it was selected and designated originally as Cal 77.32-606. It was tested later as advanced selection C5.

'Tustin' has been propagated asexually by runners and has been tested at various Univeristy of California field stations and facilities and to a very limited extent in a few growers' fields under Test Agreement.

Figure 1:
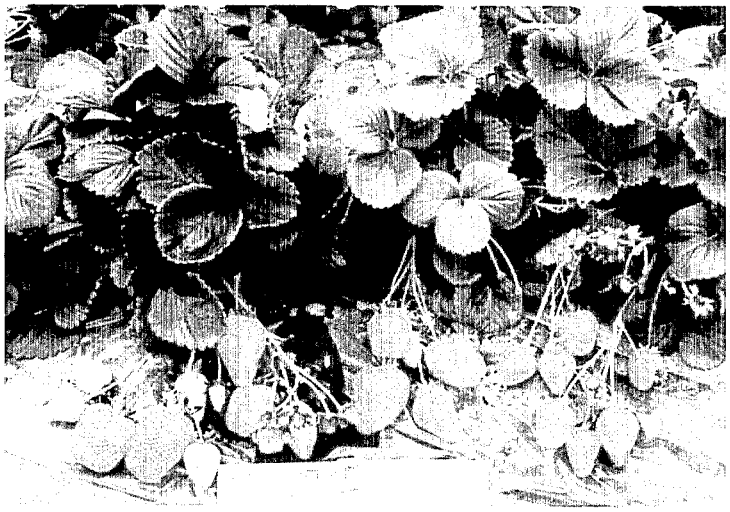
FIG. 1 shows typical growth, flowering and fruiting characteristics of the plant.
Figure 2:
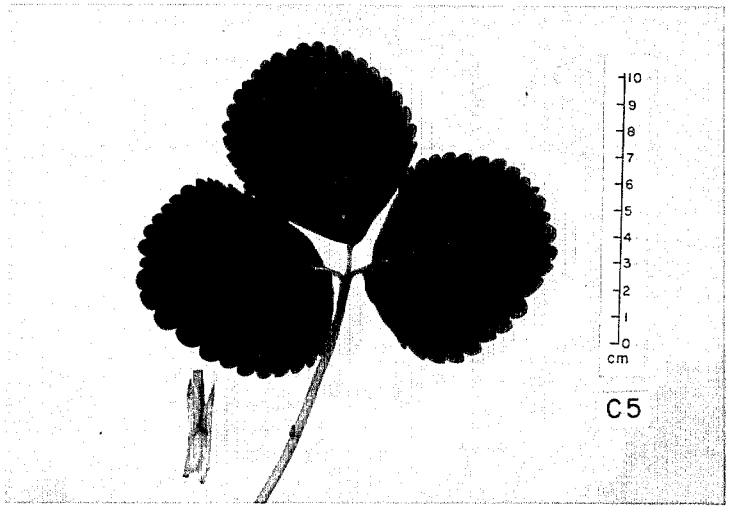
FIG. 2 shows a typical midsummer mature leaf from a plant in full fruit.
Figure 3:
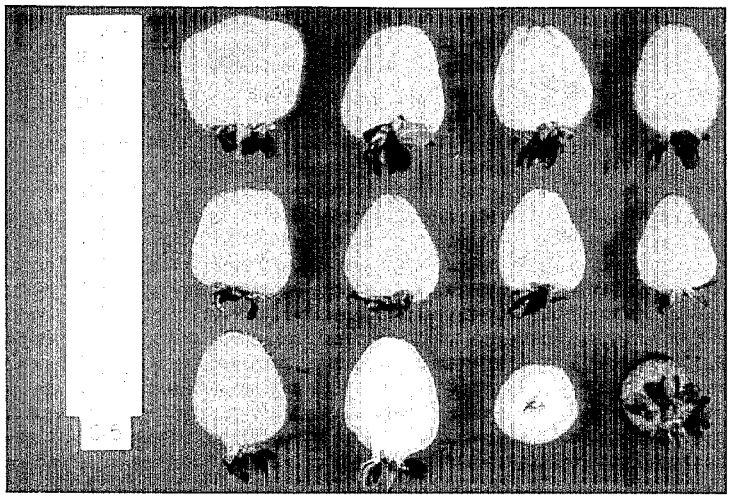
FIG. 3 shows representative early-season fruit with longitudinal and cross-sectional views.

'Tustin' is early fruiting and has performed well in winter and summer planting experiments in south and central coastal California. It is about as early as 'Tufts' or 'Tioga', later than 'Douglas'.

PLANTS AND FOLIAGE

'Tustin' plants are semicompact in growth habit, only about 75 to 85% as large as those of the standard 'Tioga' in both winter and summer plantings as estimated by measuring petiole length on plants in full fruit. Leaflets of 'Tustin' are about the same size as those of 'Tioga' averaging about 2 serrations more per terminal half leaflet. Leaves are about the same color intensity as those of 'Tioga', 2.5GY4/3 (Munsel Color System-Nickerson Color Fan). Runner production in nursery plantings is very good, better than 'Tioga'.

ISOZYMES IN LEAF EXTRACTS

'Tustin' has been classified for three enzyme systems: (A) Phosphoglucoisomerase (PGI); (B) Leucine amino peptidase (LAP); and (C) Phosphoglucomutase (PGM) making it identical to 'Aiko' but different from 'Tioga', 'Tufts', 'Pajaro' and 'Douglas' (below):

| | 'Tioga' | 'Tufts' | 'Douglas' | 'Pajaro' | 'Tustin' & 'Aiko' |
|---|---|---|---|---|---|
| PGI | A1 | A2 | A3 | A4 | A4 |
| LAP | B1 | B3 | B3 | B3 | B3 |
| PGM | C3 | C4 | C1 | C1 | C2 |

*1981 J. Amer. Soc. Hort. Sci 106:684–687.

FLOWERING AND FRUITING

'Tustin' flowers are borne on long, semi-erect peduncles which are brought down quickly by the weight of the fruit. The flowers are self fertile with ample pollen throughout the season and consequently there is little malformed fruit.

FRUIT APPEARANCE

'Tustin' fruit is blunt medium conic with some wedgy. Internally the fruit is usually slightly hollow. The fruit skin color is about 7.5R5/12 (ibid), similar to that of 'Tufts' (7.5R5.5/12). The finish is glossy and attractive. The flesh is about the same color with a light ring around the core. The achenes are bright yellow, positioned flush with surface to slightly embedded. The calyx is medium in size, borne on a short neck and reflexed. The fruit is about as firm and durable as that of 'Douglas' according to penetrometer readings and handling comparisons, softer than that of 'Tufts'. The fruit size averages much larger than that of 'Tioga' with a wider range in size as the season advances.

FRUIT QUALITY

'Tustin' has averaged about as high in ascorbic acid content as 'Tioga' (23 mg/100 g fresh fruit) as tested on summer and winter plantings during 1981 and 1982 by the method of Loeffler and Ponting (1942, J. Indust. and Engin. Chem. 14:846). Soluble solids readings were not significantly different from those of 'Tioga', 'Tufts', 'Aiko' or 'Pajaro' from comparable plantings. The flavor of 'Tustin' is excellent comparable to that of the best flavored cultivars now used in California in our opinion and according to most who have tried it. It is suitable for fresh market and processing.

We claim:

1. The new and distinct variety of strawberry plant herein described and illustrated and identified by the characteristics enumerated above.

* * * *